United States Patent [19]

Okazaki

[11] Patent Number: 5,103,805
[45] Date of Patent: Apr. 14, 1992

[54] SHOCK-WAVE CURATIVE APPARATUS
[75] Inventor: Kiyoshi Okazaki, Takanezawa, Japan
[73] Assignee: Kabushiki Kaisha Toshiba, Kawasaki, Japan
[21] Appl. No.: 579,258
[22] Filed: Sep. 5, 1990

Related U.S. Application Data

[63] Continuation of Ser. No. 458,540, Dec. 28, 1989, abandoned.

[30] Foreign Application Priority Data

Jan. 10, 1989 [JP] Japan .................... 1-3055

[51] Int. Cl.$^5$ ............................ A61B 17/22
[52] U.S. Cl. .................... 128/24 EL; 128/660.03; 128/660.09; 128/660.1
[58] Field of Search ........ 128/24 AA, 660.01, 660.03, 128/660.07, 660.08, 660.09, 660.1, 661.07, 661.09, 24 EL; 606/127, 128

[56] References Cited

U.S. PATENT DOCUMENTS

| 4,398,540 | 8/1983 | Takemura et al. | 128/661.09 |
| 4,664,121 | 5/1987 | Sanghvi et al. | 128/660.09 |
| 4,763,652 | 8/1988 | Brisson et al. | 128/24 A |
| 4,803,995 | 2/1989 | Ishida et al. | 128/24 A |
| 4,819,621 | 4/1989 | Ueberle et al. | 128/24 A |
| 4,958,639 | 9/1990 | Uchiyama et al. | 128/660.03 |
| 4,986,275 | 1/1991 | Ishida et al. | 128/660.03 |

FOREIGN PATENT DOCUMENTS

2207247 1/1989 United Kingdom .......... 128/328

Primary Examiner—Lee S. Cohen
Assistant Examiner—Krista M. Pfaffle
Attorney, Agent, or Firm—Finnegan, Henderson, Farabow, Garrett, and Dunner

[57] ABSTRACT

A shock-wave curative apparatus is provided with a second imaging probe, which is disposed outside a shock-wave applicator, in addition to a first imaging probe. The first imaging probe collects mode data of a human body, and is movably located at substantially the center of the shock-wave applicator. The second imaging probe is located outside the shock-wave applicator, and manually collects mode data of the human body from the outside of the shock-wave applicator. The first and second imaging probes are connected through a select switch to a mode data processing section. The select switch selectively makes either of the first and second imaging probes ready for use. The processed mode data is displayed by a display means.

9 Claims, 5 Drawing Sheets

SHOCK-WAVE CURATIVE APPARATUS

This application is a continuation of application Ser. No. 07/458,540 filed Dec. 28, 1989, now abandoned.

BACKGROUND OF THE INVENTION

1. Field of the Invention

The present invention relates to improvements over a shock-wave curative apparatus of the type for curing a disease caised by a calculus, whereby a calculus in a human body is disintegrated with the destroying energy of a shock wave.

2. Description of the Related Art

Figure 1:
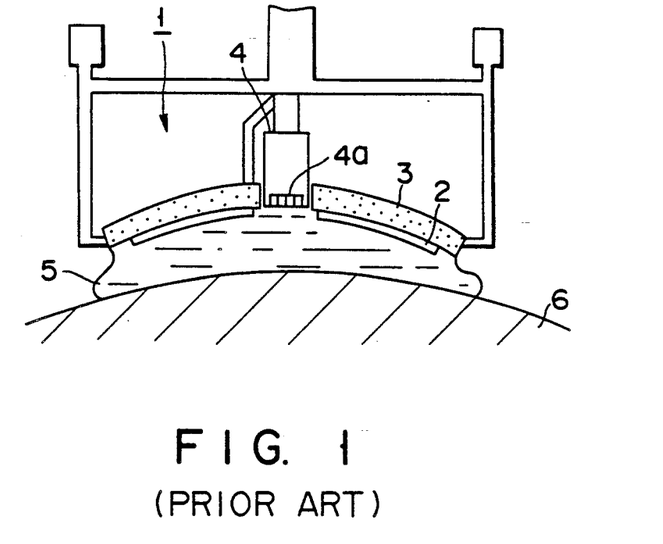
FIG. 1 schematically shows an applicator portion of a shock-wave curative apparatus of prior art.

A technique as disclosed in Japanese Patent Application Unexamined Publication No. 62-049843 is known as one of the apparatuses for disintegrating a calculus or calculuses in a human body. FIG. 1 schematically illustrates this apparatus. An applicator 1 contains a spherical transducer 2 with a curvature of 10 cm (in diameter), which has a hole of a predetermined configuration at the center, and a backing 3 uniformly layered over and bonded to the rear side of the transducer 2. An imaging probe 4 is disposed so that its transmission/reception surface 4a lies in the same plane as that in which the transmission/reception surface of the transducer 2 lies, or retracts somewhat from the plane. Reference numeral 5 designates a water bag through which a shock wave is transmitted to a human body 6.

For positioning a focal area of a shock wave, B-mode data collected by the probe 4 is visualized, and on the visualized image (B mode image), a focal area marker is set at an object to be disintegrated, e.g., a calculus. The term "focal point marker" means a focal area as geometrically determined by the applicator 1.

Use of only the visual image of the B mode data, which is collected by the probe 4 in the applicator, makes it difficult to check a location of the disintegrated object. Further, it can provide an unsatisfactory check to what degree the object is disintegrated, which follows the transmission of a shock wave. Additionally, the visual image formed by the conventional apparatus has a poor clearness.

SUMMARY OF THE INVENTION

Accordingly, an object of the present invention is to provide a shock-wave curative apparatus which may reliably and readily check a location of a disintegrated object and a degree of disintegration of the object, and further may provide a clear image of the B-mode data as collected.

To achieve the above object, there is provided a shock-wave curative apparatus comprising: shockwave applicator means having a shock-wave generating means for generating a shock wave to be focused within a human body, and a shock-wave transmitting means located closer be means for collecting mode data of a human body, the first imaging probe being movably located at substantially the center of the shock-wave applicator means; second imaging probe means located outside the shock-wave applicator means, the second imaging probe manually collecting mode data of the human body from the outside of the shock-wave applicator means; switching means coupled with the first and second imaging probe means, the switching means selectively making either of the first and second imaging probe means ready for use; mode data processing means for processing the mode data collected by the first imaging probe means and the second imaging probe means, the mode data processing means coupled through the switching means to the first and second switching means; and display means for displaying the data processed by the mode data processing means, the display means coupled with the mode data processing means.

With such an arrangement, the mode data of a human body may be collected externally by the second imaging probe, which is disposed outside the shock-wave applicator, in addition to the first imaging probe. With this and readily check a location of a disintegrated object and a degree of disintegration of the object. Additionally, the collected mode data can be clearly displayed.

DETAILED DESCRIPTION OF THE PREFERRED EMBODIMENT

A preferred embodiment of a shock-wave curative apparatus according to the present invention will be described with reference to FIGS. 2 through 9.

Figure 2:
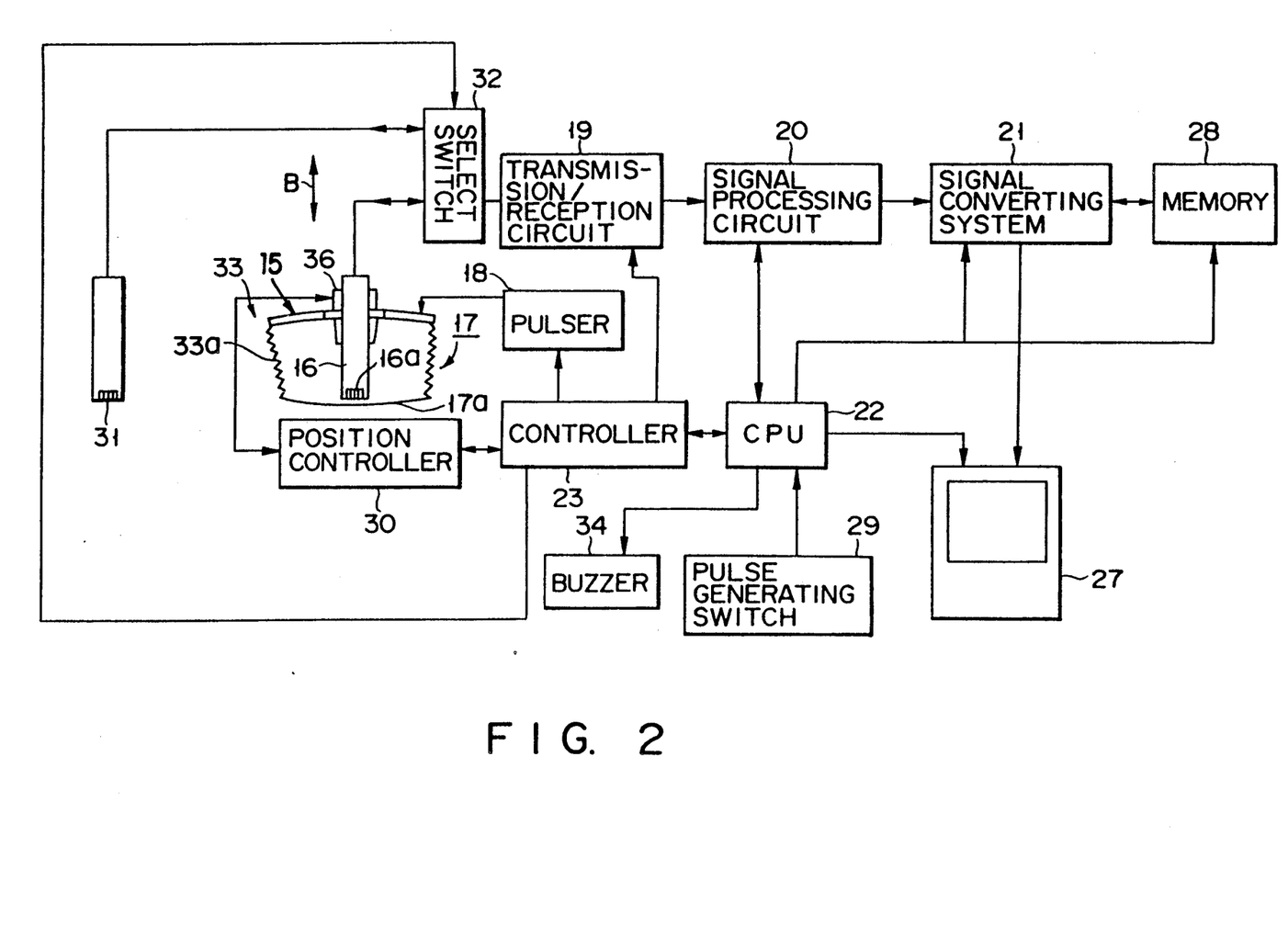
FIG. 2 is a block diagram showing a shock-wave curative apparatus according to an embodiment of the present invention.

FIG. 2 shows in block and schematic form the preferred embodiment of the curative apparatus.

Figure 3:
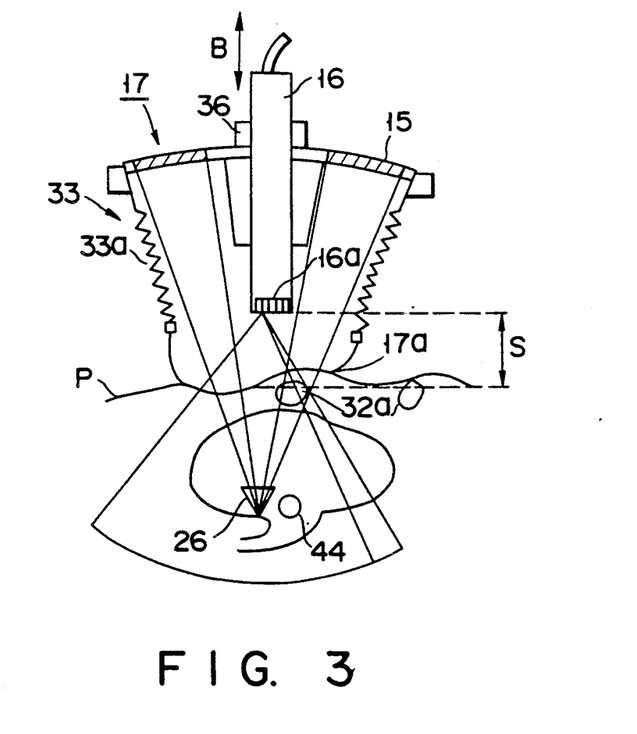
FIG. 3 shows an explanatory diagram useful in explaining a positioning control of a first probe when the curative apparatus of FIG. 1 is placed in a positioning mode.
Figure 4:
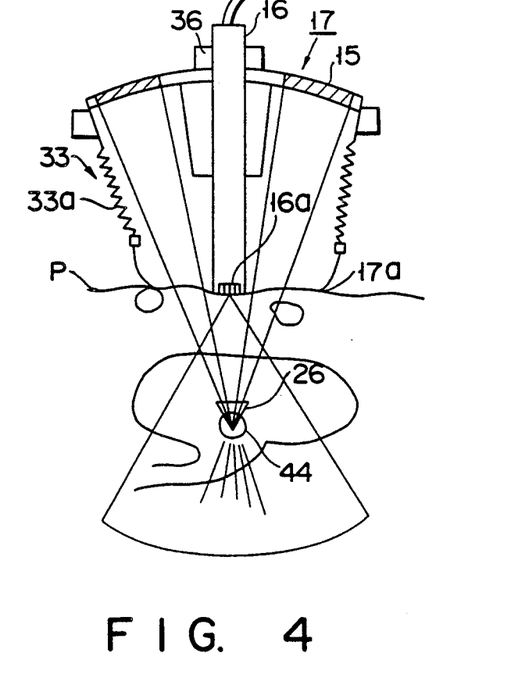
FIG. 4 shows an explanatory diagram useful in explaining a probe position in the curative apparatus when the shock-wave remedial treatment or cure is applied.

The curative apparatus is provided with a shockwave applicator 17 (referred to as an applicator), which contains a shock-wave generating means 15 for generating a shock wave, which is focused in a human body, and a shock-wave transmitting means 33, that is disposed closer to the transmission/reception surface of the transmitting means 33. The shock-wave generating means 33 may be a spherical transducer. The Shock wave transmitting means 33 may be a water bag. In the figure, reference numeral 16 designates a first imaging probe (referred to as a first probe) for collecting B mode data. The first probe 16, which is disposed at the center of the applicator 17, is vertically movable. Reference numeral 31 represents a second imaging probe (referred to as a second probe), which is disposed outside the applicator 17 and is used for collecting B mode data of a human body from the outside of the applicator 17. The second probe 31 may be a hand probe of the sector scan type. The first and the second probes 16 and 31 are coupled to a transmission/reception circuit 19, by way of a select switch 32 as a probe select means. The select switch 32 is for selecting either of the first and the second probes 16 and 31, under control of a controller 23. The transmission/reception circuit 19 transmits a pulse signal to the first probe 16 or the second probe 31, while, the transmission/reception circuit receives an echo signal of ultrasonic wave. The curative apparatus further contains a pulser 18 for transmitting a pulse signal for shock wave generation to the shock wave generating means 15, and a signal processing circuit 20, which detects an amplitude of an output signal of the circuit 19, and transmits the detected signal as a video signal to a signal converting system 21. The curative apparatus further contains a CPU (central processing unit) 22, the controller 23, the signal converting system 21, display means 27, pulse generating switch 29, and a position controller 30. The CPU 22 controls the operations of the respective units and circuits of the curative apparatus. The controller 23, under control of the CPU 22, controls the timings of transmission and reception of a pulse signal, and the amplitude and the frequency of the pulse signal in the transmission/reception circuit 19, and the signal processing circuit 20, and the pulser 18. The signal converting system 21 (digital scan converter) applies a signal converting processing to the output signals of the transmission/ reception circuit 19 and the signal processing circuit a focal area marker, and the like on the basis of the output signal of the signal converting system 21. The pulse generating switch 29 sets a timing for generating a pulse signal, which is to be transmitted to the shock-wave generating means 15. The position controller 30 adjusts a relative position of the first probe 16 with respect to the shock-wave generating means 15. The first probe 16 is moved in the direction of arrow B by means of a driver 36. The position controller 30 moves the first probe 16 in such a way that when the apparatus is in a focal-area positioning mode, the transmission/reception surface 16a of the first probe 16 is retracted from the level of the inner surface of the top end 17a of the applicator 17, as shown in FIG. 3, and after the focal-area positioning mode ends, the transmission/reception surface 16a of the first probe 16 is positioned on the level of the inner surface of the top end 17a of the applicator 17, as shown in FIG. 4. The position controller 30 and the driver 36 make up a probe movement control means in the present invention.

In the focal-area positioning mode, the CPU 22 detects a distance (stand-off length) between the transmission/reception surface of the first probe 16 and the surface of a human body. The CPU 22 detects the stand-off length on the basis of the A mode data of ultrasonic wave. Therefore, a detection of the distance in the present invention may be realized by the CPU 22 functionally. When the results of the stand-off length detectno by the CPU 22 have a value below a preset value (threshold value), a buzzer 34 is sounded. Where the stand-off length is below the threshold value, a motion of the applicator may cause the transmission/reception surface of the first probe 16 to hit a bone of a human body. To avoid such a situation, the buzzer is provided and sounds an alarm. An alarming means in the present invention may be constituted by the buzzer 34.

Reference numeral 28 designated a memory for storing a set of B mode data collected by the first probe 16 and the second probe 31. A memory means in the present invention may be constituted by this memory 28.

An operation of the curative apparatus thus arranged will be described.

To start, the second probe (hand probe) 31 is made to contact a human body. Under this condition, an ultrasonic wave is transmitted to and received from the human body through the second probe 31, thereby to collect B mode data of the human body. The B mode data collection is allowed when the select switch 32 selects the second probe 31 under control of the controller 23. Since the second probe 31 is a hand probe, the probe may readily be set at a desired location on the human body in a manual manner. Accordingly, it can be set at a location where a calculus within the human body, which is an object to be disintegrated, is best shown in the form of a B mode image. With this feature, an operator may readily check a location of the calculus within the human body, and after the disintegrating operation of the object, he may also readily check a degree of the disintegration of the calculus. The B mode data is transferred through the signal converting system 21 to the display means 27 where it is visualized. The same is also transferred to the memory 28, and stored therein.

The operator watches a B mode image (this is a B mode image based on the data collected by the second probe 31, and is referred to as a second B mode image) displayed by the display measn 27, and obtains a distance between the surface of the human body and the object. The distance may be measured with the eye by observing the B mode image on the display means 27 or it may automatically be measured by the CPU 22.

Figure 7:
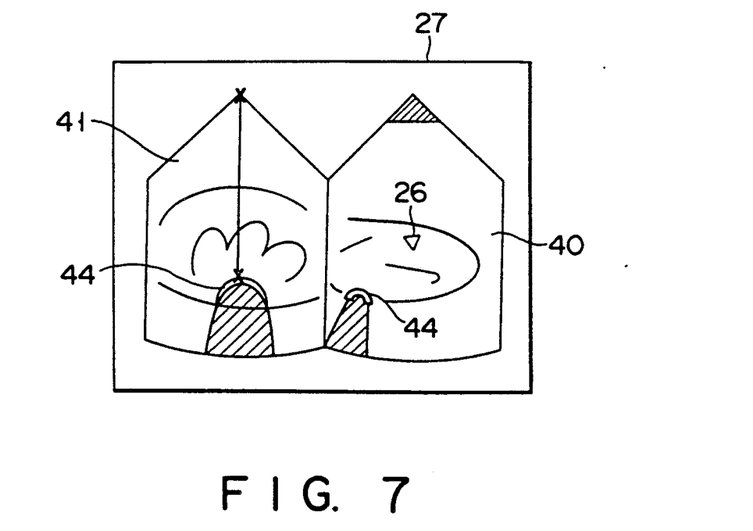
FIGS. 7 to 9 show some examples of displays of the B mode data that are displayed by a display means of the curative apparatus according to the present invention.

Then, the operator faces the shock-wave transmitting surface in the approach direction by manually operating th applicator 17. Under this condition, the second B mode image by the second probe is frozen, the first probe within the applicator 17 is selected by the select switch 32, and the transmission and reception of an ultrasonic wave to and from the human body are performed through the probe 16. The consecutive operations are done under control of the CPU 22. The B mode image (referred to as a first B mode image), which is obtained through the transmission/reception operation of the ultrasonic wave, is applied through the signal processing circuit 20 and the signal converting system 21 to the display means 27, and is displayed by the display means 27 in a real time manner. FIG. 7 exemplarily shows a display of B mode images thus obtained. In the figure, reference numeral 40 denotes a first B mode image (real time image) by the first probe 16. A marker 26a indicative of a focal area of shock wave is displayed superposed on the first B mode image 40. Reference numeral 41 represents a second B mode image (frozen image) previously obtained by the second probe 31. Reference numeral 44 designates a calculus as an object to be disintegrated.

How to position a focal area of a shock wave will be described.

Figure 8:
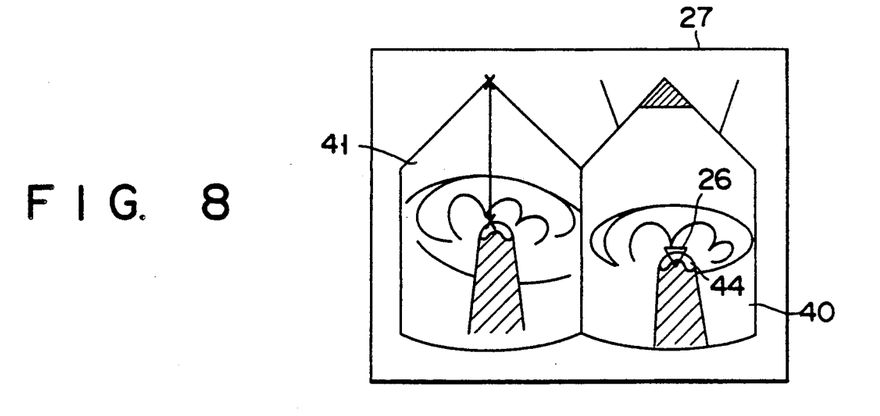

FIG. 3 shows a state of this focal area positioning. As shown, in this state, the transmission/reception surface 16a of the first probe 16 is retracted from the level of the top end inner surface 17a of the applicator 17, to form a predetermined stand-off S between the surface 16a and the surface of a human body P. Where the probe 16 is thus positioned, even if the applicator 17 is greatly moved, the surface 16a of the probe 16 will never hit a bone 32a, for example, of the human body. Accordingly, free from care of hitting the bone with the applicator, an operator may move the applicator 17, and may adjust an amount of water in the bag 33 to position the focal area 26 of the shock wave. The positioning is made by setting, on the display means 27, the focal area marker 26a at the calculus 44 as the disintegrated object on the first B mode image 40, as shown in FIG. 8.

In the positioning mode, if the stand-off S is below the predetermined value (see FIG. 3), there is a danger that the transmission/reception surface of the first probe 16 hits the bone 32a, for example, of the human body. To avoid this, the buzzer sounds an alarm. When an operator hears the alarm sound, he retracts the first probe 16 to keep the predetermined stand-off. The alarm (buzzer sound) may be generated in the following way.

The CPU 22 calculates the stand-off S from the A mode data of the ultrasonic wave, and when the stand-off S is below a preset value (stand-off threshold value), the CPU 22 sends an alarm generation signal to the buzzer 34. In response to this signal, the buzzer 34 is sounded.

After the positioning mode ends, the first probe 16 is moved down so that the transmission/reception surface 16a of the first probe 16 is positioned on the level of the top end inner surface 17a of the applicator 17. For the movement of the probe, the driver 36 is operated under control of the position controller 30. As seen from FIG. 4, showing a state of the probe after it is moved down, the transmission/reception surface 16a of the first probe 16 is in close contact with the surface of the human body P. Actually, a membrane of the water bag 33 is present between the transmission/reception surface 16a and the surface of the human body P. Under this condition, the shock wave is transmitted smoothly. That is, a shock wave generated from the shock-wave generating means 15 can be transmitted to the calculus 44 without any hindrance.

Figure 5:
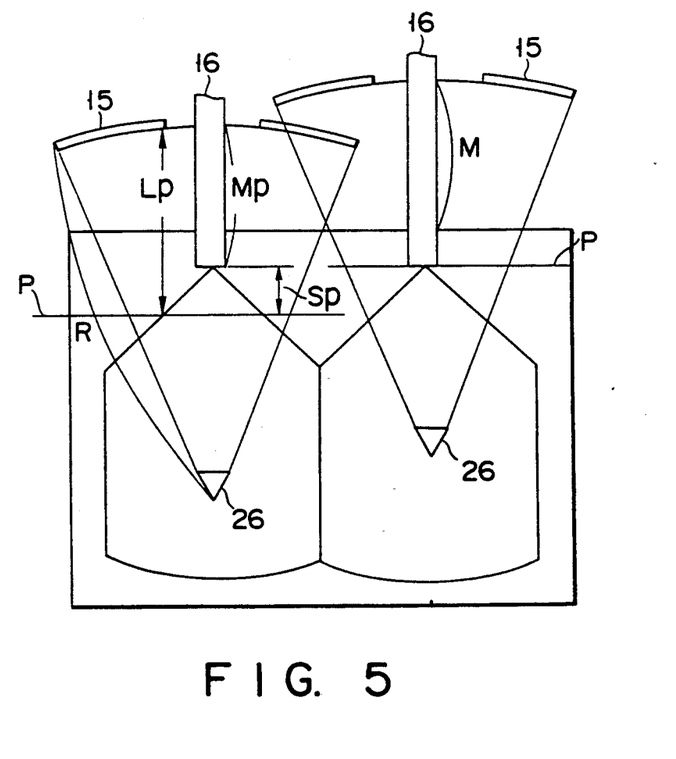
FIG. 5 shows an explanatory diagram useful in explaining how to manage a contact condition of the transmission/reception surface of the first probe with the surface of a human body.

In a curative mode, a contact condition between the surface 16a of the first probe 16 and the inner surface of the top end 17a of the applicator 17 is managed in the following way.

As shown in FIG. 5, assuming that a length of the first probe 16 (probe length) in the applicator 17 is Mp, a stand-off is S, and a correction constant is B, a contact condition CTC is $$CTC = M - (Mp + S + B) \quad (1)$$

where M indicates a probe length when the first probe 16 is in an initial state, and is variable. B indicates a depth of a depression of the surface of the human body that is caused when the surface of the human body is slightly depressed with the surface 16a of the first probe 16. Presence of the depth B provides a clear image. The contact condition when CTC=0 indicates such a state that the surface 16a of the first probe 16 is substantially in contact with the surface of the human body P, that is, the membrane of the water bag in the applicator is nipped between the surface 16a and the surface of the human body P. In a special case where the first probe 16 is turned, CTC<0 is set by lifting the first probe 16, and then CTC=0 is set by lowering the probe 16.

The management of the contact conditions as mentioned above is carried out under control of the CPU 22. When CTC>0, and a value of the CTC is below a preset value (CTC threshold value), the CPU 22 drives the buzzer 34 to issue an alarm. The CTC threshold value is selected to such an extent that a pressure by the surface 16a of the first probe 16 upon the human body will not be hard on the human body. A contact condition alarm may be provided to give an alarm when the present CTC value exceeds the CTC threshold value. In this case, the contact condition alarm and the stand-off alarm must be distinguished from each other. This may be realized by using different musical intervals or tones. To make the interval or the tone different, a frequency of an alarm generation signal is changed in accordance with the stand-off alarm or the contact condition alarm. Alternatively, two buzzers to generate sounds of different intervals or tones are provided. A contact detecting means in the present invention may be realized by the CPU 22, and the like.

A measurement of a stand-off S by using A mode data will be performed in the following way.

Figure 6:
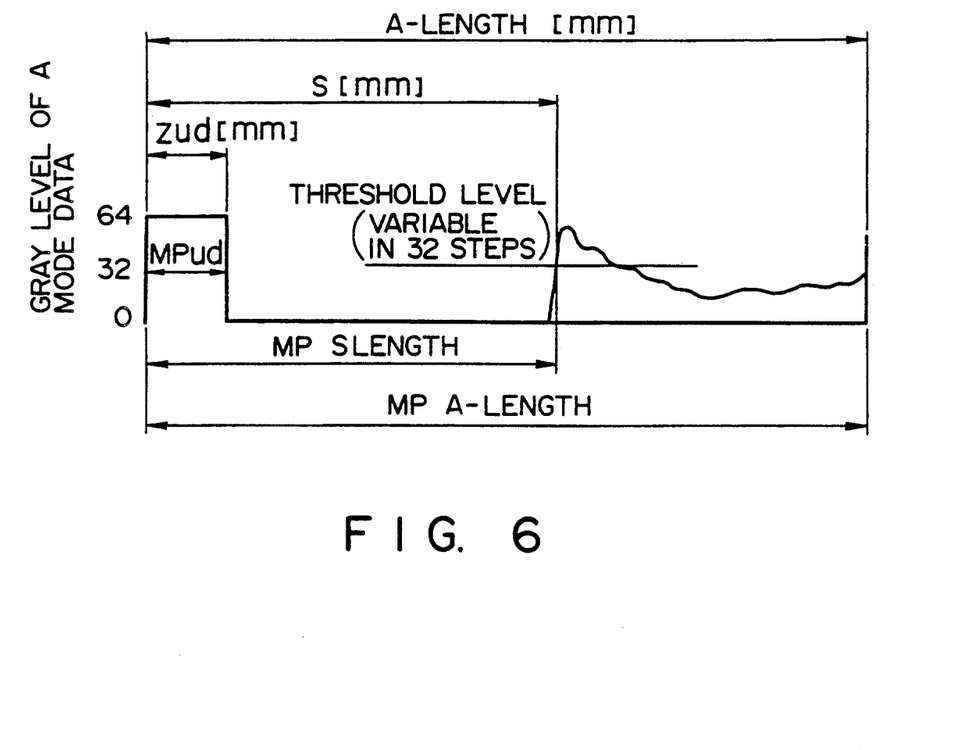
FIG. 6 graphically illustrates a relationship of a grey level of A mode data vs. stand-off length when A mode data is collected.

In FIG. 6, A-LENGTH indicates a length of A mode data, and Zud, an A mode insensitive region. A standoff of 5 mm or less cannot be measured because the insensitive region is present.

A real length Δpix per pixel [mm/pixel] is $$\Delta pix = \frac{1530 \times 10^3}{2} \cdot \frac{1}{fs} = \frac{C_0}{2 \cdot fs} \quad (2)$$

where fs = sampling frequency.

An insensitive pixel length MPud is expressed by $$MPud = \frac{Zud}{\Delta pix}$$

Accordingly, a stand-off length S [mm] is $$S = MP_{slength} \cdot \Delta pix.$$

Figure 9:
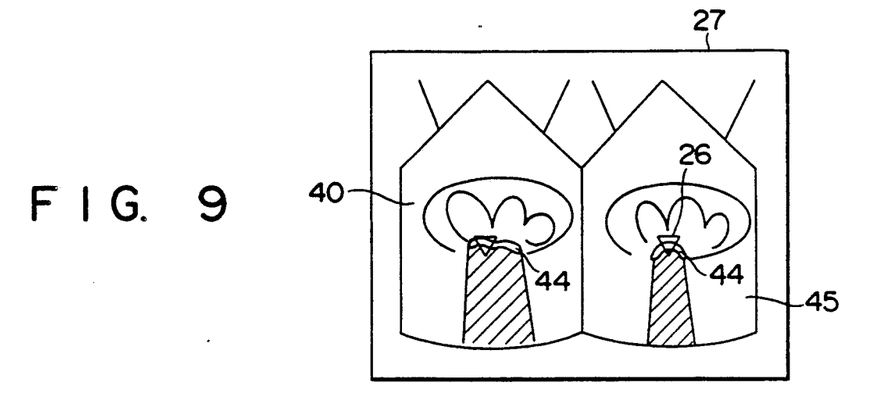

The shock wave transmission follows the completion of the focal area positioning. Before the shock wave transmission starts, the first B mode image 40, instead of the second B mode image 41, is frozen and displayed as shown in FIG. 9. In the figure, an image designated by reference numeral 40 is a first B mode image as is frozen, and an image denoted as 41 is a real time second B mode image.

The generation of a shock wave starts upon the turning on of the pulse generating switch 29. When the switch 29 is turned on, the CPU 22 recognizes the turn-on of the switch 29. Under control of the controller 23, the pulser 18 produces a drive pulse toward the shock wave generating means 15. Upon receipt of the drive pulse, the shock wave generating means 15 transmits a pulse, the shock wave toward the disintegrated object 44 in the human body P. The shock wave is focused at the focal area 26. Accordingly, if, as a result of the positioning, the object 44 is coincident with the focal area 26, the object 44 is disintegrated with the disintegrating energy of the shock wave. It is noted here that the real time second B mode image 41 by the frozen first probe 16 in the applicator 17 and the first B node image 45 of the object before the shock wave is transmitted, are concurrently displayed on the display means 27, as shown in FIG. 9. Therefore, if those images are comparatively watched and studied, a degree of disintegration, or the result of remedial treatment, can be checked readily.

If required, the second probe 31 may be replaced with another type of probe, for example, a convex probe or a linear probe, and a B mode image based on the B mode data collected by the new probe is displayed. Since a field of view differs with the probe used, replacement of the probe will provide a more proper check of the result of the treatment. In this case, a B mode image (also categorized into the second B mode image) by the convex probe or the linear probe is image is frozen and displayed as a freeze image.

In the curative apparatus of the instant embodiment, the B mode image is stored in the memory 28. Accordingly, if required later, it may be read out of the memory and displayed. This enables an operator to re-check the result of the cure.

While the present invention has been described using a specific embodiment, the present invention may variously be modified within the scope of the present invention.

Figure 10:
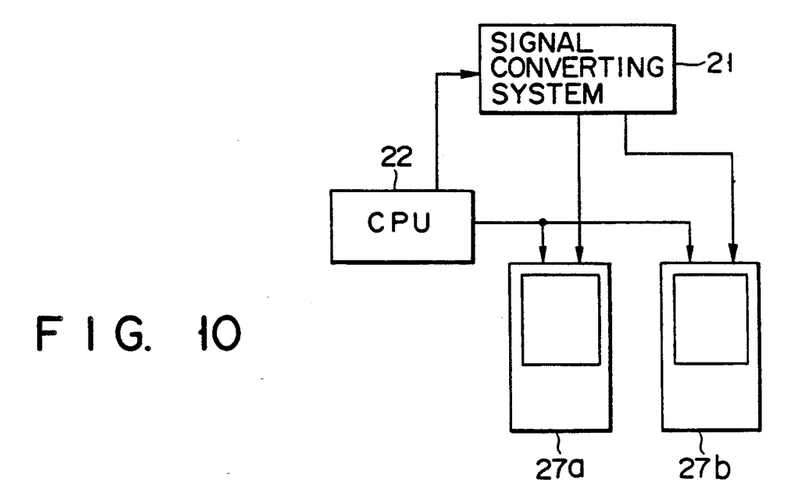
FIG. 10 shows a block diagram of a modification of the embodiment of FIG. 2, which the display means is modified.

For example, in the above-mentioned embodiment, the first and the second B mode images are displayed on the same display screen. Alternatively, two display means 27a and 27b may be used, as shown in FIG. 10, one for displaying the first B mode image, and the other for displaying the second B mode image.

Further, the shock wave generating means 15 may be realized by a suitable means, for example, a generating means of the electromagnetic induction type.

What is claimed is:

1. A shock-wave curative apparatus, comprising:
shock-wave applicator means having a shock-wave generating means for generating a shock wave to be focused within a human body, and transmitting means for transmitting the shock wave;
first imaging probe means movable within said shock-wave applicator means, for collecting mode data of a human body;
second imaging probe means external to the shock-wave applicator means, for manually collecting mode data of the human body external to said shock-wave applicator means;
switching means coupled with said first and second imaging probe means, for selectively making either of said first or second imaging probe means ready for use;
mode data processing means coupled through said switching means to said first and second imaging probe means, for processing the mode data collected by said first and said second imaging probe means;
image data freezing means for freezing the processed mode data collected by said second imaging probe means when both the mode data collected by said first imaging probe means and the mode data collected by said second imaging probe means are to be displayed; and
display means for displaying the mode data collected by said first imaging probe mans and processed by said mode data processing means, and for displaying the mode data frozen by said image freezing means.

2. The apparatus according to claim 1, wherein said mode data processing means includes a memory means for storing said mode data collected by said first and second imaging probe means.

3. The apparatus according to claim 1, wherein the shock wave generating means includes an inner surface, the first imaging probe means includes a transmission/reception surface, and the apparatus further comprises probe movement control means for positioning said first imaging probe means such that the transmission/reception surface is retracted from the inner surface when the first imaging probe means is in a focal area marker positioning mode wherein a focal area marker is positioned on the display means, and movably controlling said first imaging probe means for contacting the transmission/reception surface with the inner surface after the focal area marker has been positioned.

4. The apparatus according to claim 1, wherein the first imaging probe means includes a transmission/reception surface, and said mode data processing means includes means for detecting a distance between the transmission/reception surface and a surface of the human body when the first imaging probe means is in a focal area marker positioning mode wherein a focal area marker is positioned on the display means, and means for giving an alarm when the distance detected by said distance detecting means is below a preset value.

5. The apparatus according to claim 1, wherein said display means comprises a single display screen for displaying the mode data collected by said first imaging probe means and the mode data collected by said second imaging probe means.

6. The apparatus according to claim 1, wherein said display means includes a firs display screen for displaying the mode data collected by said first imaging probe means and a second display screen for displaying the mode data collected by said second imaging probe means.

7. A shock-wave curative apparatus, comprising:
shock-wave applicator means for generating a shock wave to be focused within a human body, and transmitting means for transmitting the shock wave;
first imaging probe means movable within said shock-wave applicator means, the first imaging probe means having a transmission/reception surface, for collecting mode data of the human body;
second imaging probe means external to the shock-wave applicator means, for manually collecting mode data of the human body external to said shock-wave applicator means;
switching means coupled with said first and second imaging probe means, for selectively making either of said first or second imaging probe means ready for use;
mode data processing means coupled through said switching means to said first and second imaging probe means, for processing the mode data collected by said first and said second imaging probe means, said mode data processing means including means for detecting a distance between the transmission/reception surface of said first imaging probe means and a surface of the human body when the first imaging probe means is in a focal area marker positioning mode,
first alarm generating means for giving an alarm when the distance detected by said distance detecting means is below a preset distance value,
contact condition detecting means for detecting a contact condition result value of the degree of contact of the transmission/reception surface with the surface of the human body, and
second alarm generating means for giving an alarm when the contact condition result value is below a preset contact condition result value;
image data freezing means for freezing the processed mode data collected by said second imaging probe means when both the mode data collected by said first imaging probe means and the mode data collected by said second imaging probe means are to be displayed; and display means coupled to said mode data processing means and said image freezing means, for displaying the mode data collected by said first imaging probe means and processed by said mode data processing means, and for displaying the mode data frozen by said image freezing means.

8. The apparatus according to claim 7, wherein said display means comprises a single display screen for displaying both the mode data collected by said first imaging probe means and the mode data collected by said second imaging probe means.

9. The apparatus according to claim 7, wherein said display means includes a first display screen for displaying the mode data collected by said first imaging probe means and a second display screen for displaying the mode data collected by said second imaging probe means.

* * * * *

UNITED STATES PATENT AND TRADEMARK OFFICE
CERTIFICATE OF CORRECTION

PATENT NO. : 5,103,805
DATED : April 14, 1992
INVENTOR(S) : Kiyoshi OKAZAKI It is certified that error appears in the above-identified patent and that said Letters Patent is hereby corrected as shown below:

Claim 1, column 7, line 51, change "mans" to --means--.

Claim 6, column 8, line 20, change "firs" to --first--.

Signed and Sealed this

Twenty-sixth Day of October, 1993

Attest:

BRUCE LEHMAN

*Attesting Officer*   *Commissioner of Patents and Trademarks*